United States Patent [19]
Israel

[11] Patent Number: 6,139,145
[45] Date of Patent: Oct. 31, 2000

[54] OPHTHALMIC OPTICAL ELEMENT INCORPORATING A HOLOGRAPHIC ELEMENT AND USE OF SAME IN CASES OF CENTRAL FIELD LOSS

[76] Inventor: Henry M. Israel, 39 Ben-Zakai, 51482 Bnei-Brak, Israel

[21] Appl. No.: 09/190,209

[22] Filed: Nov. 13, 1998

[51] Int. Cl.[7] ............................... G02C 7/04; G02C 7/06; G02B 5/32

[52] U.S. Cl. ..................... 351/160 R; 351/159; 351/161; 351/168; 351/177; 359/19

[58] Field of Search ................................ 351/161, 160 B, 351/160 H, 177, 162; 359/19

[56] References Cited

U.S. PATENT DOCUMENTS

| | | | |
|---|---|---|---|
| 4,642,112 | 2/1987 | Freeman | 351/161 |
| 5,100,226 | 3/1992 | Freeman | 351/161 |
| 5,760,871 | 6/1998 | Kosoburd et al. | 351/161 |
| 5,997,140 | 12/1999 | Zhang et al. | 351/161 |

*Primary Examiner*—Scott J. Sugarman
*Attorney, Agent, or Firm*—Mark M. Friedman

[57] ABSTRACT

A method of correcting vision defects associated with central field loss. The method is effected by passing light arriving at a retina of an eye through an image deflection ophthalmic optical element including a lens body, the lens body including a lens portion for focusing light entering the eye and a prismatic holographic element being in context with the lens portion, the prismatic holographic element being for deflecting the light entering the eye to off a center of the retina.

19 Claims, 5 Drawing Sheets

OPHTHALMIC OPTICAL ELEMENT INCORPORATING A HOLOGRAPHIC ELEMENT AND USE OF SAME IN CASES OF CENTRAL FIELD LOSS

FIELD AND BACKGROUND OF THE INVENTION

The present invention relates to ophthalmic optical elements incorporating a image deflecting/magnifying holographic element and, more particularly, to the use of such ophthalmic optical elements positioned within the eye, in intimate contact with the eye, or in front of the eye, for correction of vision defects, central field loss, such as macular degeneration, in particular. The invention further relates to a system for determining an optimal angle to which an image is to be deflected by corrective optics for enabling optimal vision in central vision loss conditions.

As shown in FIG. 1, a normal eye 10 includes a cornea 12, an aqueous solution called the aqueous humor 14 behind cornea 12, an iris 16, a natural lens 18, ciliary sulcus 20, retina 22, macula 24 at the center of the retina, and fovea 26 at the center of macula 24. The cornea 12 and lens 18 cause an image 30 to form at fovea 26. Fovea 26 is a circular zone approximately 0.2–0.5 $mm^2$ in area. The image 30 formed at fovea 26 corresponds to a locus of fixation for providing acute vision. This locus of fixation helps to coordinate voluntary and involuntary head and eye movements required for daily activities, such as reading, driving, and dressing. Peripheral images are located around this locus of fixation.

A common cause of blindness in adults is macular degeneration. This retinal disease involves damage to the fovea so that the fovea is unable to process images. The blind spot is located at the center of a patient's visual field. The patient is thus unable to read, drive, or perform other tasks that require the brain to reference the locus of fixation.

In most patients, even in those with advanced macular degeneration, the macula is not completely damaged, but retains healthy areas. However, the loss of the locus of fixation caused by the central blind zone leads to severe visual impairment and often to legal blindness, defined as visual acuity of 20/200 or less. The number of patients diagnosed with such severe visual impairment in the United States alone exceeds 2 million.

Intraocular lens implants have been devised to replace the natural lens of the eye and restore sight to damaged or diseased eyes. For example, compound intraocular lenses that combine different optical elements have been proposed. In such proposals, a diffractive/refractive lens implant includes a diffractive lens profile covering about half the effective lens area. Such a configuration allows about half of the incident light from distant objects and half of the incident light from near objects to enter the eye. Such a compound optic provides an ability to form on the retina a focused image of both distant objects and near objects.

Although both images are formed on the fovea, the brightness of the image in each case is reduced by about 50%, or the ratio of the light intensity assigned to each image. In certain cases, such a lens can be used to treat macular degeneration by providing sufficient image magnification so as to project the image over a retinal area more than that damaged by macular degeneration. Such an approach, however, does not shift the image to healthy portions of the retina.

Similar multifocal intraocular lenses incorporating two refractive zones also have been disclosed. For example, the use of a pair of bifocal intraocular lenses has been disclosed in which each of the pair of bifocal intraocular lenses incorporates a refractive element and a diffractive element. One of the lenses provides greater image intensity for the image of near objects, while the other lens provides greater image intensity for the image of distant objects. This approach has the advantage that the incident light can be apportioned or split between the two images in a continuous manner between the two lenses. The disadvantage is that the image is processed by two optical elements, each of which introduces its own aberrations and loss of image contrast so that the performance of the compound lens can be worse than either a diffractive or refractive lens.

Intraocular lenses incorporating a single refractive element also have been devised to shift the image from a damaged portion of the retina to a healthy area. In this respect, a prismatic intraocular lens that includes a convex lens portion for focusing light rays and a prism posterior to the convex lens for deflecting light away from the diseased center of the retina to a functional portion. The prismatic intraocular lens restores the central field vision to a patient.

Several considerations arise before such a prismatic intraocular lens can be prescribed for a patient suffering central field loss. For example, means to fixate the intraocular lens in the eye has to be developed in order to ensure that the lens does not rotate or tilt. Such displacements would cause the shifted retinal image to move, perhaps back to a zone which has become nonfunctional due to macular degeneration. It may also damage the eye tissue. In addition, due to the geometry of the eye, it is necessary to minimize the deepness of the prism wedge while remaining deep enough to redirect an image to a desired location on the retina.

Accordingly, U.S. Pat. No. 5,683,457 to Gupta et al. teaches a pair of intraocular lenses for restoring visual function to a patient with central field loss. The pair of intraocular lenses includes a first lens for implantation into a first eye of the patient to provide vision of targets located at a distance greater than five feet from the first eye and a second lens for implantation into a second eye of the patient to provide vision of targets at a distance less than twelve inches from the second eye. The first and second lenses each include a prismatic wedge for shifting retinal images to a functional portion of a retina of each respective first and second eye.

Similarly, U.S. Pat. No. 4,581,031 to Koziol discloses an intraocular lens including a convex portion and a prismatic portion for use with patients having macular degeneration of the retina. The lens is to be implanted in the eye, after removal of the natural lens, to direct rays of light away from the diseased center of the retina and focus them on a non-affected area of the retina, thereby improving sight. The lens includes a lens portion having a first portion including means for focusing light entering the eye and a second portion including prism means for deflecting light entering the eye away from the center of the retina. The lens further includes means, coupled to the lens portion, for supporting the lens portion in the eye.

The disadvantages of the teachings by Gupta et al. and Koziol are that the deepness and weight of the lenses employed cause inaccurate placement and positional instability resulting in impaired vision and, in severe cases, damage to surrounding eye tissue and post operative need to remove, reposition or change the lens.

It will be appreciated that an equivalent device can be configured as a contact lens. However, the deepness of the prismatic lens will not allow proper eye motion or response to blinking.

There is thus a widely recognized need for, and it would be highly advantageous to have, a holographic ophthalmic element which is thin and light weight in nature, which can be used inter- or intra-ocularly in cases of central field loss, such as macular degeneration, and which avoids the limitations of the prior art described herein.

SUMMARY OF THE INVENTION

Thus, it is among the objectives and advantages of the present invention to overcome the drawbacks and deficiencies of the prior art and to provide inter- and intra-ophthalmic image deflection optical elements which incorporate a prismatic holographic element, preferably a deep, blazed, transmission hologram, possessing different defractive powers and prismatic properties effective over the visible spectrum, such combinations so as to provide image deflection within the eye, using bifocal or multifocal configurations, on or off the macula.

It is among the additional objectives and advantages of the present invention to provide an image deflection intraocular lens assembly, wherein image deflection activity is provided by a prismatic holographic element, preferably a deep, blazed, transmission hologram, thus reducing the size and weight of the image deflection intraocular lens assembly, enabling the assembly to be inserted in the eye through a small incision, placed properly within the eye and being stable in the presence of the natural motion of the eye.

It is among the additional objectives and advantages of the present invention to provide an image deflection contact lens assembly, wherein image deflection activity is provided by a prismatic holographic element, preferably a deep, blazed, transmission hologram, thus reducing the size and weight of the prismatic contact lens assembly and allowing the device to have smooth surfaces, enabling the device to remain stable on the eye in the presence of eye motion and blinking.

It is among the additional objectives and advantages of the present invention to provide an image deflection spectacles assembly, wherein image deflection activity is provided by a holographic element, preferably a deep, blazed, transmission hologram, thus reducing the size and weight of the spectacles.

It is among the additional objectives and advantages of the present invention to provide a method and device to measure the required prismatic deflection for the holographic element, or any other prismatic element.

It is among the objectives and advantages of the present invention to overcome the drawbacks and deficiencies of the prior art and to provide inter- or intra-ophthalmic magnifying optical elements which incorporate a magnifying holographic element, preferably a deep, blazed, transmission hologram, possessing different defractive powers and combinations of defractive powers effective over the visible spectrum, such combinations so as to provide image magnification within the eye optimized over a range of distances, using bifocal or multifocal configurations, on or off of the macula.

It is among the additional objectives and advantages of the present invention to provide a magnifying intraocular lens assembly, wherein image magnification is provided by a combination of a refractive lens and a magnifying holographic element, preferably a deep, blazed, transmission hologram, thus reducing the size and weight of the magnifying intraocular lens assembly, enabling the assembly to be inserted in the eye through a small incision, placed properly within the eye and being stable in the presence of the natural motion of the eye.

It is among the additional objectives and advantages of the present invention to provide a magnifying contact lens assembly, wherein image magnification is provided in part by a magnifying holographic element, preferably a deep, blazed, transmission hologram, thus reducing the size and weight of the magnifying contact lens assembly and allowing the assembly to have smooth surfaces enabling the assembly to remain stable on the eye in the presence of eye motion and blinking.

It is among the additional objectives and advantages of the present invention to provide a magnifying spectacles assembly, wherein image magnification is provided in part by a magnifying holographic element, preferably a deep, blazed, transmission element, thus reducing the size and weight of the magnifying spectacles assembly.

Thus, according to one aspect of the present invention there is provided a method of correcting vision defects associated with central field loss. The method comprising the steps of passing light arriving at a retina of an eye through an image deflection ophthalmic optical element including a lens body, the lens body including a lens portion for focusing light entering the eye and a prismatic holographic element being in context with the lens portion, the prismatic holographic element being for deflecting the light entering the eye to off a center of the retina.

According to another aspect of the present invention there is provided an intraocular image deflection ophthalmic optical element adapted to be implanted in the eye. The ophthalmic optical element comprising a lens body including a lens portion for focusing light entering the eye and a prismatic holographic element being in context with the lens portion, the prismatic holographic element being for deflecting the light entering the eye to a desired location on the retina.

According to further features in preferred embodiments of the invention described below, the intraocular image deflection ophthalmic optical element further comprising a mechanism for engaging and supporting the ophthalmic optical element within the eye, the mechanism being coupled to the lens body.

According to yet another aspect of the present invention there is provided an interocular image deflection ophthalmic optical element adapted to be in intimate contact with the eye. The ophthalmic optical element comprising a lens body including a lens portion for focusing light entering the eye and a prismatic holographic element being in context with the lens portion, the prismatic holographic element being for deflecting the light entering the eye to a desired location on the retina.

According to still another aspect of the present invention there is provided an interocular image deflection ophthalmic optical element adapted to be worn in front of the eye. The ophthalmic optical element comprising a lens body including a lens portion for focusing light entering the eye and a prismatic holographic element being in context with the lens portion, the prismatic holographic element being for deflecting the light entering the eye to a desired location on the retina.

According to yet another aspect of the present invention there are provided spectacles comprising a frame and at least one interocular image deflection ophthalmic optical element as set forth hereinabove.

According to still further features in the described preferred embodiments the prismatic holographic element being for deflecting the light entering the eye off a center of the retina.

According to still further features in the described preferred embodiments the prismatic holographic element being for deflecting the light entering the eye to a center of the retina.

According to still further features in the described preferred embodiments the prismatic holographic element is a deep, blazed transmission hologram.

According to still further features in the described preferred embodiments the prismatic holographic element also serves for image magnification.

According to still further features in the described preferred embodiments the lens portion also serves for image magnification.

According to still further features in the described preferred embodiments the prismatic holographic element also serves as a plurality discrete focal element.

According to still further features in the described preferred embodiments the lens portion also serves as a plurality discrete focal element.

According to still further features in the described preferred embodiments the prismatic holographic element also serves as a multifocal element.

According to still further features in the described preferred embodiments the lens portion also serves as a multifocal element.

According to still another aspect of the present invention there is provided an intraocular image magnification ophthalmic optical element adapted to be implanted in the eye. The ophthalmic optical element comprising a lens body including a lens portion for focusing light entering the eye and a magnifying holographic element being in context with the lens portion, the magnifying holographic element being for magnifying the light image entering the eye.

According to further features in preferred embodiments of the invention described below, the intraocular image magnification ophthalmic optical element further comprising a mechanism for engaging and supporting the ophthalmic optical element within the eye, the mechanism being coupled to the lens body.

According to yet another aspect of the present invention there is provided an interocular image magnification ophthalmic optical element adapted to be in intimate contact with the eye. The ophthalmic optical element comprising a lens body including a lens portion for focusing light entering the eye and a magnifying holographic element being in context with the lens portion, the magnifying holographic element being for magnifying the light image entering the eye.

According to yet another aspect of the present invention there is provided an interocular image magnification ophthalmic optical element adapted to be worn in front of the eye. The ophthalmic optical element comprising a lens body including a lens portion for focusing light entering the eye and a magnifying holographic element being in context with the lens portion, the magnifying holographic element being for magnifying the light image entering the eye.

According to still another aspect of the present invention there are provided spectacles comprising a frame and at least one interocular image magnification ophthalmic optical element as set forth hereinabove.

According to still further features in the described preferred embodiments the magnifying holographic element is a deep, blazed transmission hologram.

According to still further features in the described preferred embodiments the magnifying holographic element also serves for image deflection.

According to still further features in the described preferred embodiments the magnifying holographic element also serves as a plurality discrete focal element.

According to still further features in the described preferred embodiments the lens portion also serves as a plurality discrete focal element.

According to still further features in the described preferred embodiments the magnifying holographic element also serves as a multifocal element.

According to still further features in the described preferred embodiments the lens portion also serves as a multifocal element.

According to yet another aspect of the present invention there is provided a system for determining an optimal angle to which an image is to be deflected by corrective optics for enabling optimal vision in central vision loss conditions, the system comprising (a) an array of individually operable visual light sources; (b) a source of electromagnetic radiation reflectable from an eye; (c) a detector for detecting electromagnetic radiation being reflected from the eye; and (d) a processor communicating with the detector and with the array of individually operable visual light sources for determining an angle of deflection of the eye when viewing any one of the individually operable visual light sources, to thereby determine the optimal angle to which an image is to be deflected by corrective optics for enabling optimal vision in central vision loss conditions.

According to still further features in the described preferred embodiments the electromagnetic radiation is infrared radiation and further wherein the detector is an infrared sensitive detector.

The present invention successfully addresses the shortcomings of the presently known configurations by providing effective solutions to central vision loss conditions and other conditions associated with suboptimal vision.

BRIEF DESCRIPTION OF THE DRAWINGS

The invention herein described, by way of example only, with reference to the accompanying drawings, wherein.

DESCRIPTION OF THE PREFERRED EMBODIMENTS

Figure 1:
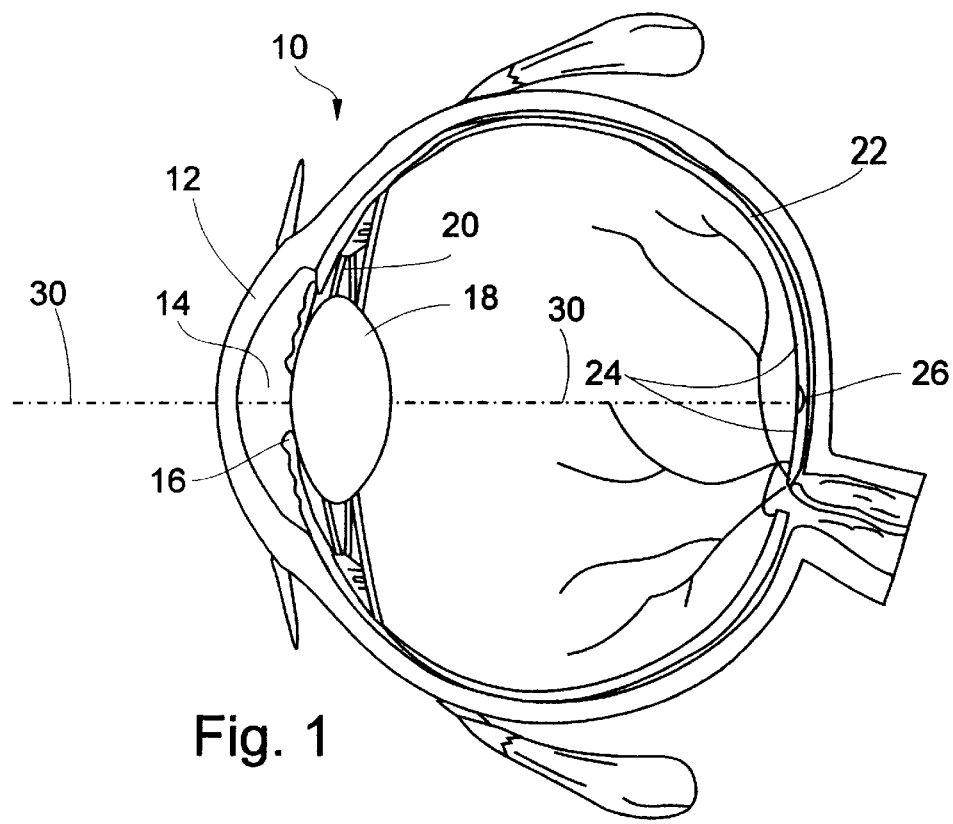
FIG. 1 is a cross sectional view of a human eye.

The present invention is of ophthalmic optical elements incorporating a image deflecting/magnifying holographic element which can be used to correct vision defects. Specifically, the present invention can be used to correct or improve central field vision loss resulting from, for example, macular degeneration.

The principles and operation of the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Figure 2:
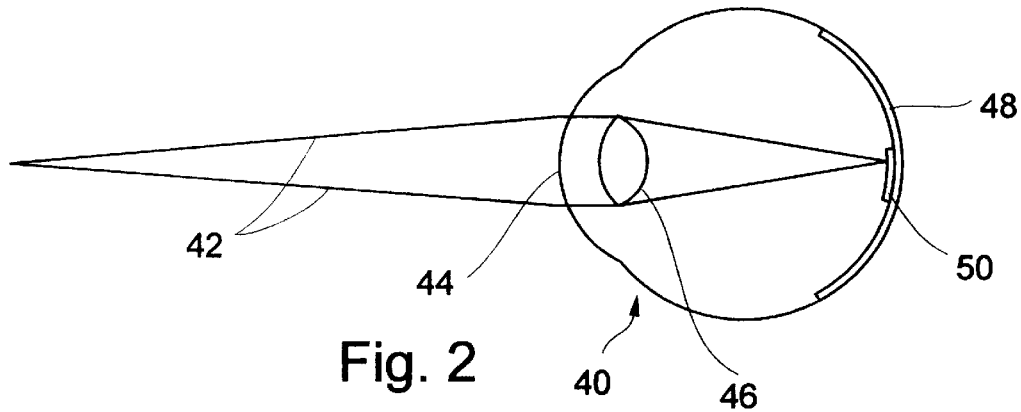
FIG. 2 is a schematic cross sectional depiction of the optics associated with normal eye operation.

Referring now to the drawings, FIG. 2 illustrates the basic components and the optics of an eye 40. Light rays 42 are diffracted once while passing the cornea 44 and then while passing the natural eye lens 46 to thereafter focus on the light sensitive cells present in the back wall of the eye, known as the retina 48. Substantially in its center, the retina 48 includes a region of high resolution known as the macula 50. The macula 50 is located at the center of the retina 48, approximately five degrees off of the central optical axis of the eye. The macula 50 provides high definition vision and acuity, both required for every day life. The retina 48 provides lower resolution vision. As already mentioned, light rays 42 are focused on the macula 50 by means of the cornea 44 and the lens 46. Thus, the optical power of the eye is derived from the average 40 diopters of the cornea 44 and an additional 20 diopters of the lens 46 for a total of 60 diopters. Thus, light rays 42 entering the eye on the visual axis are focused on the macula 50 and provide high definition vision. By contrast light rays entering the eye off of the visual axis provide lower acuity. However, when the macula 50 degenerates, high definition vision and central vision are lost or severely degraded.

Accordingly, the present invention is aimed, in one aspect, at providing efficient means of deflecting the light rays away from the diseased macula and to thereby focus the light rays on a non-diseased area of the retina.

Thus, according to one aspect of the present invention there is provided a method of correcting vision defects associated with central field loss. The method is effected by passing light arriving at a retina of an eye through an image deflection ophthalmic optical element including a lens body. The lens body includes a lens portion for focusing light entering the eye and a prismatic holographic element being in context with the lens portion. The prismatic holographic element being for deflecting the light entering the eye off a center of the retina, i.e., off the macula, such that the image is deflected to a non-degenerated region of the retina. As further detailed hereinunder, the method according to the present invention can be effected by a variety of image deflection ophthalmic optical elements, including, but not limited to, ophthalmic optical elements adapted to be implanted in the eye, ophthalmic optical elements adapted to be in intimate contact with the eye (contact lenses), or ophthalmic optical elements adapted to be worn in front of the eye (spectacles).

Figure 3:
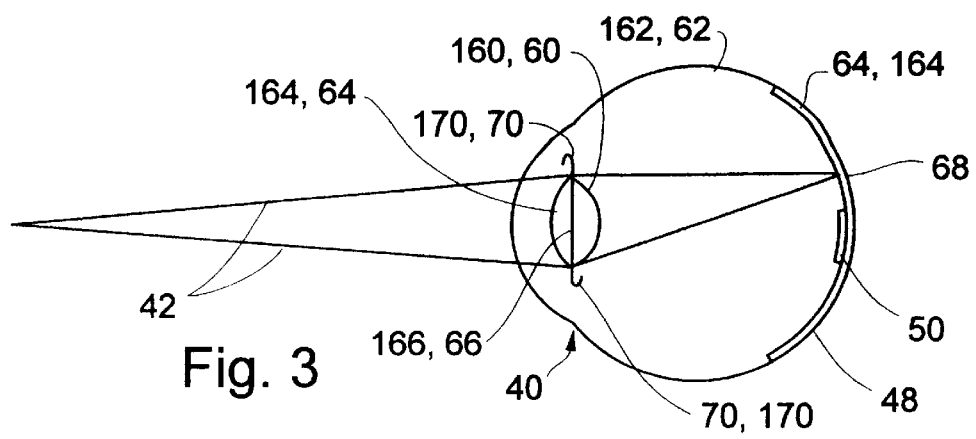
FIG. 3 is a schematic cross sectional depiction of the optics associated with intraocular image deflection ophthalmic optical element adapted to be implanted in an eye according to the present invention.
Figure 4:
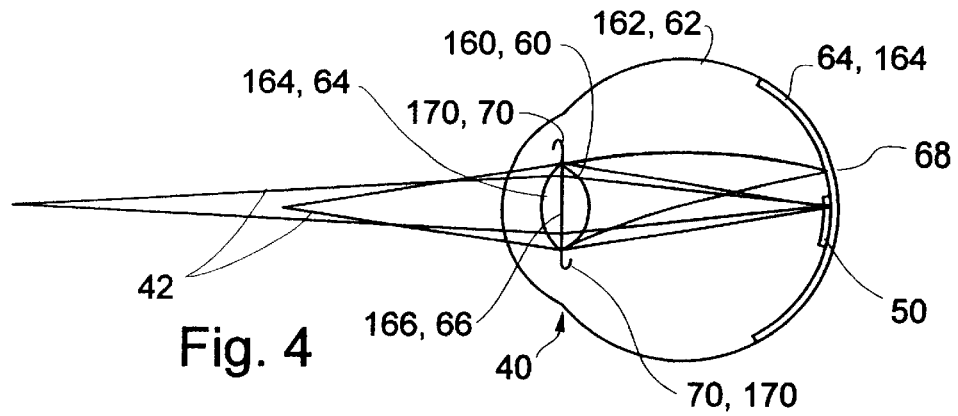
FIG. 4 is a schematic cross sectional depiction of the optics associated with intraocular ophthalmic optical element adapted to be implanted in an eye according to the present invention and provide bifocality.
Figure 5:
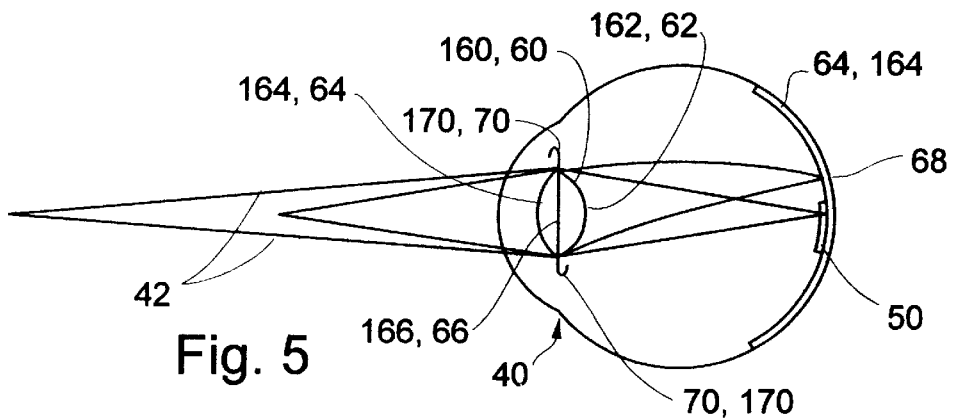
FIG. 5 is a schematic cross sectional depiction of the optics associated with intraocular ophthalmic optical element adapted to be implanted in an eye according to the present invention and provide multifocality.

Thus, as shown in FIG. 3–5, according to one embodiment of the present invention an intraocular image deflection ophthalmic optical element 60 adapted to be implanted in the eye is provided. Typically, element 60 is designed to replace the natural lens of the eye. Ophthalmic optical element 60 includes a lens body 62. Lens body 62 includes a lens portion 64, ground or molded from any suitable optical material, for focusing light 42 entering the eye, and a prismatic holographic element 66 which is in context with lens portion 64. By "being in context" it is meant—being connected to, integrally formed with, incorporated in, etc. Prismatic holographic element 66 serves for deflecting light 42 entering the eye to a desired location, say 68, on retina 48. Lens portion 64 provides the mechanical strength for holding holographic element 66. Lens portion 64 is preferably made from a flexible material such that element 60 as a whole can be rolled, collapsed or folded and thereby incorporated into the eye via a small incision.

Thus, holographic element 66 provides a prismatic activity which can be used to deflect light 42 from the visual axis. As further detailed below, it may also provide additional optical power as a fixed, multifocal, bifocal and or magnifying lens, although, yet less preferably, also lens portion 64 can be designed to comply with these optical tasks. It is advantageous to include most of the optical power in holographic element 66 to thereby keep the overall size and shape of element 60 constant, regardless of its optical behavior.

According to a preferred embodiment of the present invention, intraocular image deflection ophthalmic optical element 60 further includes a mechanism 70 for engaging and supporting ophthalmic optical element 70 within the eye. Mechanism 70 is coupled to lens body 62. U.S. Pat. No. 4,418,431 to Feaster and U.S. Pat. No. 5,683,457 to Gupta et al., both incorporated by reference as if fully set forth herein, teach a mechanism for engaging and supporting an ophthalmic optical element within the eye, which is therefore not further described herein.

Figure 6:
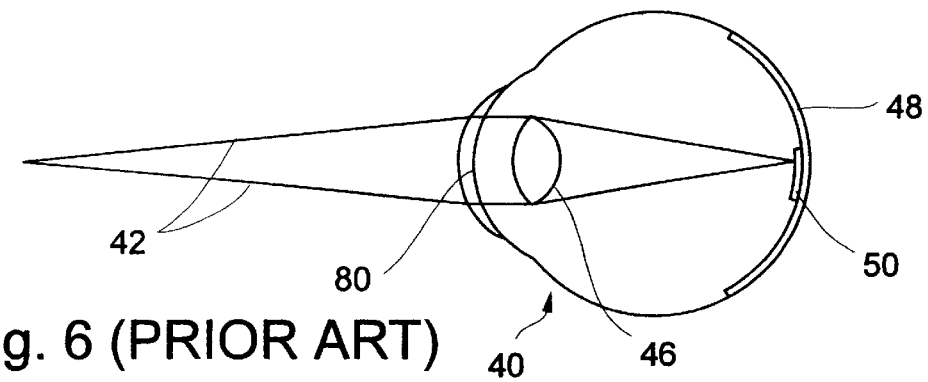
FIG. 6 is a schematic cross sectional depiction of a prior art contact lens.
Figure 7:
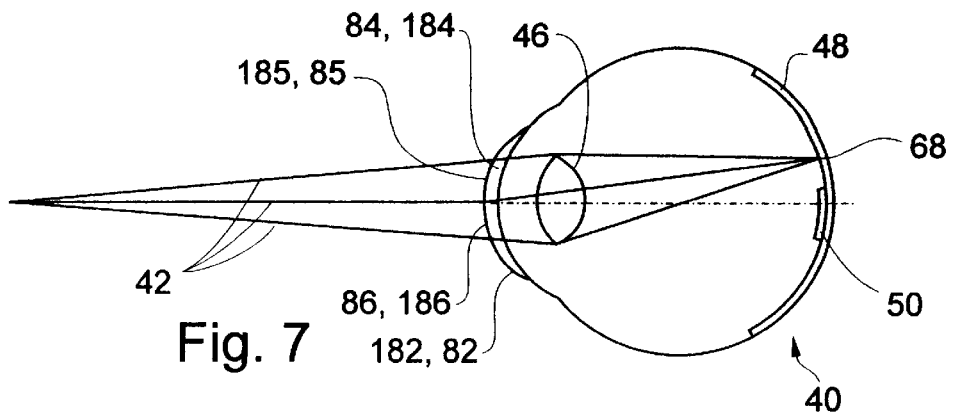
FIG. 7 is a schematic cross sectional depiction of the optics associated with an image deflection interocular ophthalmic optical element adapted to be implanted in intimate contact with an eye according to the present invention.
Figure 8:
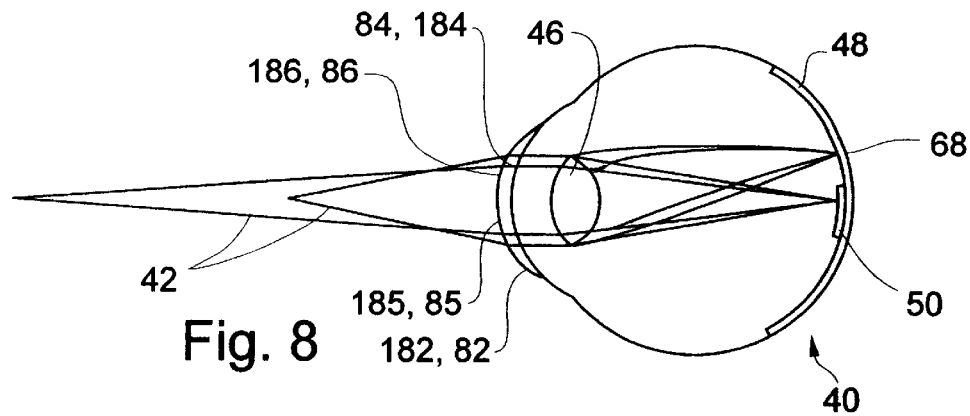
FIG. 8 is a schematic cross sectional depiction of the optics associated with an interocular ophthalmic optical element adapted to be implanted in intimate contact with an eye according to the present invention and provided with bifocality.
Figure 9:
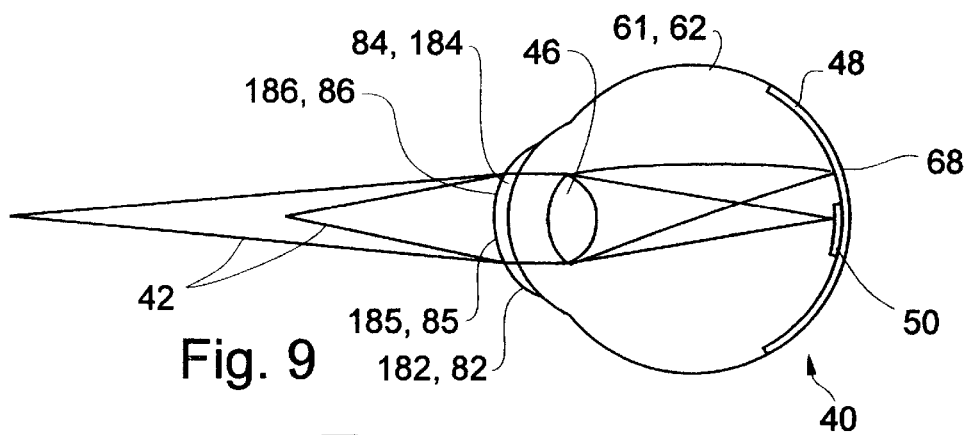
FIG. 9 is a schematic cross sectional depiction of the optics associated with an interocular ophthalmic optical element adapted to be implanted in intimate contact with an eye according to the present invention and provided with multifocality.

FIG. 6 shows a prior art contact lens 80 positioned externally in intimate contact with the eye. FIGS. 7–9 show an interocular image deflection ophthalmic optical element 82 according to another aspect of the present invention. Element 82 is adapted to be in intimate contact with the eye, like a prior art contact lens. Ophthalmic optical element 82 includes a lens body 84 including a lens portion 85 for focusing light 42 entering the eye, and a prismatic holographic element 86 which is in context with lens portion 84. Prismatic holographic element 86 serves for deflecting light 42 entering the eye to a desired location, say 68, on retina 68.

Figure 10:
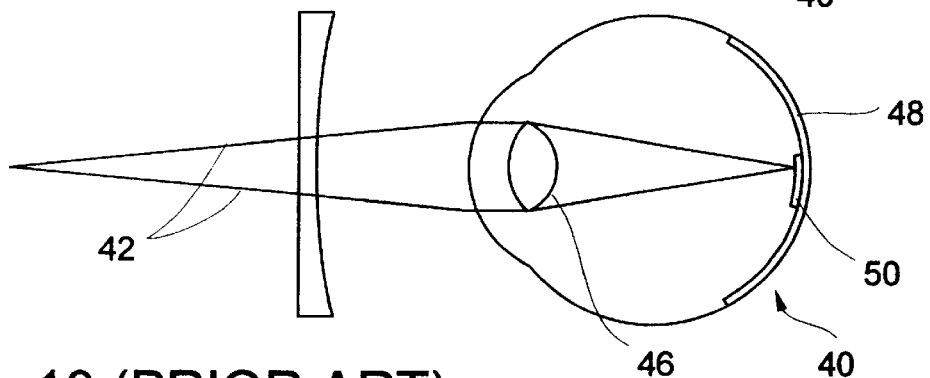
FIG. 10 is a schematic cross sectional depiction of a prior art lens of spectacles.
Figure 11:
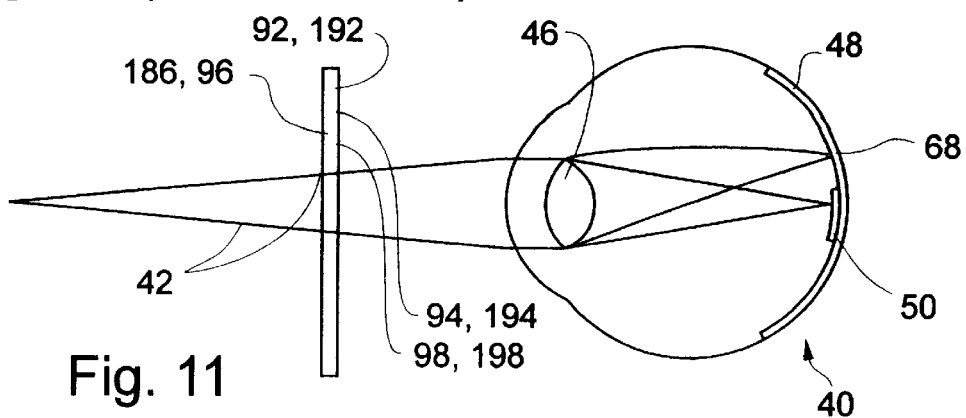
FIG. 11 is a schematic cross sectional depiction of the optics associated with an interocular ophthalmic optical element adapted to be implanted in front of the eye according to the present invention.
Figure 13:
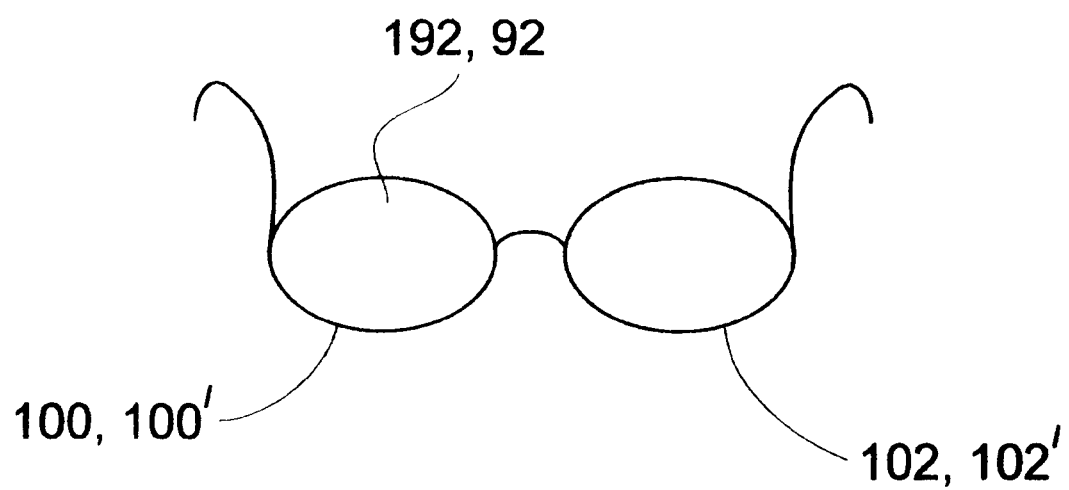
FIG. 13 show spectacles according to the present invention.

FIG. 10 shows a prior art spectacles lens 90 positioned in front of the eye. FIG. 11 shows an interocular image deflection ophthalmic optical element 92, according to another aspect of the present invention, adapted to be worn in front of the eye, in a fashion similar to a spectacles lens. Ophthalmic optical element 92 includes a lens body 94 including a lens portion 96 for focusing light 42 entering the eye, and a prismatic holographic element 98 which is in context with lens portion 96. Prismatic holographic element 98 serves for deflecting light 42 entering the eye to a desired location on retina 48. As shown in FIG. 13, according to yet another aspect of the present invention there are provided spectacles 100. Spectacles 100 include a frame 102 and at least one interocular image deflection ophthalmic optical element 92 as set forth hereinabove. Spectacles 100 preferably includes arms 102 engagable behind the ears, for supporting spectacles 100 in front of the eyes of the user, as well known in the art.

According to preferred embodiments of the present invention, prismatic holographic element 66, 86 or 98 serves for deflecting light 42 entering the eye off a center of the retina, i.e., of the diseased macula 50. Yet, for some applications it may be desirous that prismatic holographic element 66, 86 or 98 will serve for deflecting the light entering the eye to the center of the retina, i.e., onto a healthy macula 50.

According to another preferred embodiments of the present invention prismatic holographic element 66, 86 or 98 is a deep, say about 2 μm, blazed transmission hologram, effective in transmitting light of the entire visual spectrum. However, it will be appreciated that for some application, monochromatic or achromatic transmission holograms can be employed. U.S. Pat. No. 5,680,231 to Grinberg et al., which is incorporated by reference as if fully set forth herein, teaches a deep, blazed, transmission holographic element effective for wavelengths of the visual spectrum.

However, according yet another preferred embodiments of the present invention prismatic holographic element 66, 86 or 98 and/or lens portion 64, 85 or 96 also serves for image magnification. Magnifying lenses and transmission holograms are well known in the art and require no further description herein.

As demonstrated in FIGS. 4–5 and 8–9, according to prismatic holographic element 66, 86 or 98 and/or lens portion 64, 85 or 96 also serves as a plurality discrete focal (e.g., bi- or tri-focal) element or as a multifocal element. Plurality discrete and multi focal lenses and transmission holograms are well known in the art and require no further description herein.

FIGS. 3–5, 7–9, 11 and 13 will now be used to described several additional aspects and embodiments of the present invention. These aspects and embodiments of the present invention can find uses for correcting or relieving a variety of vision defects.

Thus, referring again to FIGS. 3–5, according to still another aspect of the present invention there is provided an intraocular image magnification ophthalmic optical element 160 adapted to be implanted in the eye. The ophthalmic optical element includes a lens body 162 including a lens portion 164 for focusing light entering the eye and a magnifying holographic element 166 which is in context with lens portion 164. Magnifying holographic element 166 serves for magnifying the light image entering the eye. Intraocular image magnification ophthalmic optical element 160 preferably further includes a mechanism 170 for engaging and supporting ophthalmic optical element 160 within the eye. Mechanism 170 is coupled to lens body 162.

Referring again to FIGS. 7–9, according to still another aspect of the present invention there is provided an interocular image magnification ophthalmic optical element 182, adapted to be in intimate contact with the eye. Ophthalmic optical element 182 includes a lens body 184 including a lens portion 185 for focusing light entering the eye, and a magnifying holographic element 186 which is in context with lens portion 185. Magnifying holographic element 186 serves for magnifying the light image entering the eye.

Referring again to FIG. 11, according to yet another aspect of the present invention there is provided an interocular image magnification ophthalmic optical element 192, adapted to be worn in front of the eye. The ophthalmic optical element includes a lens body 194, including a lens portion 196 for focusing light entering the eye, and a magnifying holographic element 198 which is in context with lens portion 196. Magnifying holographic element 198 serves for magnifying the light image entering the eye. As shown in FIG. 13, according to yet another aspect of the present invention there are provided spectacles 100'. Spectacles 100' include a frame 102' and at least one interocular image deflection ophthalmic optical element 192 as set forth hereinabove.

According to another preferred embodiments of the present invention magnifying holographic element 166, 186 or 198 is a deep, say about 2 μm, blazed transmission hologram, effective in transmitting light of the visual spectrum. However, it will be appreciated that for some application, monochromatic or achromatic transmission holograms can be employed.

According to still another preferred embodiments of the present invention magnifying holographic element 166, 186 or 198 also serves for image deflection.

According to still another preferred embodiments of the present invention magnifying holographic element 166, 186 or 198 and/or lens portion 164, 185 or 196 also serves as a plurality discrete focal element or as a multifocal element.

In the case of macular degeneration, the location of the point of fixation needs to be measured and a corrective device fitted. The evaluation of the proper functionality of the corrective device is subjective. Only the patient knows if it works. According to the prior art, to measure the angle of the point of fixation, there are two possibilities:

With a scanning laser ophthalmoscope (SLO) it is possible to map the retina. By projecting a target onto the retina it is possible to locate a fixation area relative to the test fixture. It is not possible, however, to locate a fixation point in an eye coordinate system with the SLO measurement.

With a modified eye tracking system it is possible to measure the eye fixation angle. By projecting a target onto the retina it is possible find the fixation angle, in three space, relative to a construction plane containing the pupillary opening of the iris. Projection of a target will allow the patient to fixate on the target. The eye tracker will measure the angle that the eye takes to fixate on the target. Repetition of this procedure will establish the pupil shape, the fixation angle and map the field of view.

Figure 12:
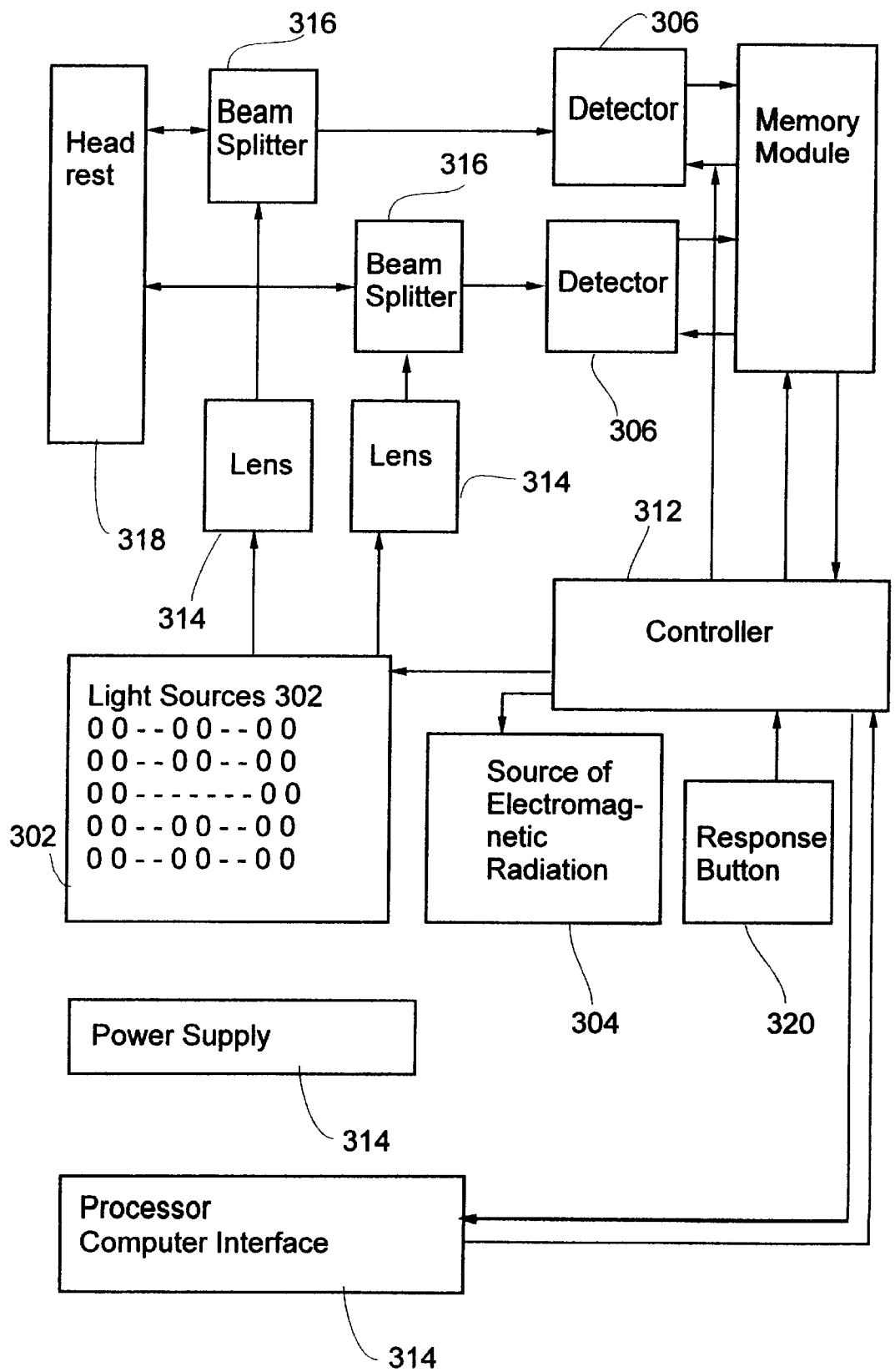
FIG. 12 is a block diagram of a system for determining an optimal angle to which an image is to be deflected by corrective optics for enabling optimal vision in central vision loss conditions according to the present invention.

Referring now to FIG. 12. According to yet another aspect of the present invention there is provided a system for determining an optimal angle to which an image is to be deflected by corrective optics for enabling optimal vision in central vision loss conditions.

In order to test the eye for field of view the eye is forced to fixate on a central location and light sources are illuminated one at a time over the expected field of view and a response is when the light source is perceived. This test does not record the eye gaze angle or point to point eye motion, rather data is discarded if and when the gaze angle goes off of the fixation point. There are a number of eye abnormalities or diseases in which there is only visual perception off of the central gaze angle and the intent is to measure the field of view and gaze angle offset of these abnormal and deceased eyes to allow proper visual correction.

The base measurement is to fixate the eye on a central point, zero gaze angle offset, and observe the shape of the pupil followed by fixation at angles offset from the zero gaze angle and record the pupil shape.

From the assembled data the actual pupil shape can be ascertained at zero gaze offset. The pupil shape is then used to calculate the angular offset of the eye from the zero offset position for each test angle of the illumination source.

The offset of the utilized visual field is then determined, the corrected visual field data determined and the a proper correction angle determined with respect to the plane of the pupil.

This correction angle has been determined from data with respect to the pupil and therefore are in self consistent eye coordinates and can be utilized to properly fit a corrective device to the eye.

The system can also be utilized for the measurement of normal field of view by fixating the eye on the central point and soliciting a response by the illumination light sources over the field of view. The response can be in a variety of forms: manual response by pushing a switch, pupil reflex response by measurement of the pupil diameter change or nerve response by measurement of the electrical potential produced by the optic nerve and sensed through contacts on the skin.

To determine the angle to which the image is to be deflected by corrective optics a system 300, such as that shown in FIG. 12 can be employed. System 300 includes an array of individually operable visual light sources 302. System 300 further includes a source of electromagnetic radiation 304 reflectable from an eye, say infrared radiation. System 300 further includes a detector 306 (preferably two, one for each eyes) for detecting electromagnetic radiation being reflected from the eye, say an infrared radiation sensitive detector. System 300 further includes a processor including a computer interface 308 for commanding system 300, a memory module 310 for storing data for later retrieval, a controller 312 for controlling the operation of system 300 and coordinating the operation of its other components, a power supply 314 for providing system 300 with power for its operation, an optical arrangement including a lens 314 (preferably two, one for each eye) and a beam splitter 136 (preferably two, one for each eye) for positioning light sources 303 on the optical axis of detector 306, while, at the same time permitting passage of electromagnetic radiation produced by source 304 and reflected from the eye to detector 306, a ahead rest 318 on which the examined patient rests his head during the examination process and which positions the eye or eyes thereof on the optical axis or axes of detector or detectors 306, and a response button 320 through which the examined individual reports when he sees best one of light sources 302 presently illuminating.

System 300 serves for determining an angle of deflection of the eye relative to the optical axis of the eye which is normal to the iris and pupil opening when viewing any one of the individually operable visual light sources 302, to thereby determine the optimal angle to which an image is to be deflected by corrective optics for enabling optimal vision in central vision loss conditions.

The operation thereof is as follows. The examined patient rests his head on head rest 318. The source of electromagnetic radiation is turned on, such that detector 306 is capable of determining the angle of deflection of the eye at all times. Then, one of light sources 302 is turned on. The patient is told to tilt his eyes for best perception of that light source 302 and then, when best perception is obtained, to indicate system 300 that this is the case, by pressing response button 320. Thus, when pressed, response button 320 reports system 300 that an angle of optimal fixation has been achieved by the patient. At that point, detector 306 is requested for the angle of deflection of the eye during optimal fixation. It will be appreciated by one ordinarily skilled in the art, that reporting system 300 that an angle of optimal fixation has been achieved by the patient can be effected not only by button 320, but, alternatively, by the pupil reflex or nerve response. In any case, repeating the above process with different light sources 302, operated at different times, and correlating between the location of operated sources 302 on the array and the corresponding deflection of the eye at fixation, enables to determine the spot on the retina to which light is to be deflected for optimal vision and to design corrective optics thereto.

It will be appreciated by one ordinarily skilled in the art that system 300 can be provided in a miniaturized head mounted configuration. Using such a configuration obviates the need to either correct for head movements or restrain head movements during examination, and further obviates the need for large space, darkened area and the like.

The present invention enjoys numerous advantages over the prior art. According to the present invention defractive technology is applied to treat or relieve maculopathies of different etiologies and other applications. The fundamental idea is to place a holographic optical element on or into the eye to correct the defective condition. The use of holographic technology allows the element to be smaller and light weight and allows programmable element modification in both optical field modification and color correction.

The application of a holographic element to a contact lens as described herein provides a solution with complete ease of adjustment and modification. The use of a hard prism ballast lens or a soft bevel fix "C" holds the contact lens in a near fixed location on the cornea. The motion of such a contact lens caused by blinking is acceptable in that the lens returns to a position on the cornea which would allow a holographic prism on the lens to place the image repeatedly on a usable portion of the retina with acceptable accuracy. U.S. Pat. No. 5,235,441 to Georgaras, describes holographic spectacles and the process of their manufacture. A similar process can be used to manufacture either intra or interocular elements as described herein. It will be appreciated that deep holograms are not limited to flat surfaces. The addition of optical magnification either fixed or as a bifocal or multifocal adds an additional advantage to the present invention. Furthey (Furthey, Holographic Optics: Optically and Computer generated, Proc. SPIE Vol. 1052, pp. 142–149 (1989): "Defractive bifocal intraocular lens") has shown that it is possible to construct a deep holographic bifocal element on the flat posterior surface of an intraocular lens. The present holographic elements can be constructed on any surface and unlike Freeman's elements (U.S. Pat. Nos. 4,641,934 and 4,642,112 and Freeman, Stone, Transaction of the British Contact Lens Association Conference 1987: "A New Diffractive Bifocal Contact Lens") which are color dependent, the deep hologram functions over the full color range of the eye.

As will be appreciated by those skilled in the art, the optical elements used according to the present invention can be achieved in practice through the use of suitable non spherical surfaces or narrow band holographic elements in which different light wavelengths are bent and used to form images at different angles or distances. It is also to be understood that color dependence of the eye lens can be corrected through use of the holograms to form achromatic optical elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. An interocular image deflection ophthalmic optical element adapted to be in intimate contact with an eye of a patient suffering macular degeneration and having a retina, the ophthalmic optical element comprising a lens body including a lens portion for focusing all visible light entering the eye and a prismatic holographic element being in context with said lens portion, said prismatic holographic element being for deflecting said light entering the eye off a center of the retina, so as to deflect an entire scene off said center of the retina and improve eyesight in cases of macular degeneration.

2. The interocular image deflection ophthalmic optical element of claim 1, wherein said prismatic holographic element is a deep, blazed transmission hologram.

3. The interocular image deflection ophthalmic optical element of claim 1, wherein said prismatic holographic element also serves for image magnification.

4. The interocular image deflection ophthalmic optical element of claim 1, wherein said lens portion also serves for image magnification.

5. The interocular image deflection ophthalmic optical element of claim 1, wherein said prismatic holographic element also serves as a plurality discrete focal element.

6. The interocular image deflection ophthalmic optical element of claim 1, wherein said lens portion also serves as a plurality discrete focal element.

7. The interocular image deflection ophthalmic optical element of claim 1, wherein said prismatic holographic element also serves as a multifocal element.

8. The interocular image deflection ophthalmic optical element of claim 1, wherein said lens portion also serves as a multifocal element.

9. A method of correcting vision defects associated with macular degeneration comprising the steps of passing all visible light arriving at a retina of an eye through an image deflection ophthalmic optical element including a lens body, said lens body including a lens portion for focusing all visible light entering the eye and a prismatic holographic element being in context with said lens portion, said prismatic holographic element being for deflecting said light entering the eye to off a center of the retina, so as to deflect an entire scene off said center of the retina and improve eyesight in cases of macular degeneration.

10. The method of claim 9, wherein said image deflection ophthalmic optical element is adapted to be implanted in the eye.

11. The method of claim 9, wherein said image deflection ophthalmic optical element is adapted to be worn in front of the eye.

12. The method of claim 9, wherein said image deflection ophthalmic optical element is adapted to be in intimate contact with the eye.

13. The method of claim 9, wherein said prismatic holographic element is a deep, blazed transmission hologram.

14. The method of claim 9, wherein said prismatic holographic element also serves for image magnification.

15. The method of claim 9, wherein said lens portion also serves for image magnification.

16. The method of claim 9, wherein said prismatic holographic element also serves as a plurality discrete focal element.

17. The method of claim 9, wherein said lens portion also serves as a plurality discrete focal element.

18. The method of claim 9, wherein said prismatic holographic element also serves as a multifocal element.

19. The method of claim 9, wherein said lens portion also serves as a multifocal element.

* * * * *